(12) United States Patent
Hu

(10) Patent No.: US 10,508,070 B1
(45) Date of Patent: Dec. 17, 2019

(54) METHOD FOR PREPARING 3-HYDROXYBUTYRATE SALTS

(71) Applicant: SHANGHAI SHINE HIGH INTERNATIONAL TRADE CO., LTD., Shanghai (CN)

(72) Inventor: Yanwang Hu, Shanghai (CN)

(73) Assignee: SHANGHAI SHINE HIGH INTERNATIONAL TRADE CO., LTD., Shanghai (CN)

( * ) Notice: Subject to any disclaimer, the term of this patent is extended or adjusted under 35 U.S.C. 154(b) by 0 days.

(21) Appl. No.: 16/233,657

(22) Filed: Dec. 27, 2018

(30) Foreign Application Priority Data

Nov. 28, 2018 (CN) .......................... 2018 1 1432860

(51) Int. Cl.
| | | |
|---|---|---|
| *C07C 51/09* | (2006.01) | |
| *C07C 51/44* | (2006.01) | |
| *C07C 51/41* | (2006.01) | |
| *B01J 23/04* | (2006.01) | |
| *C07C 59/01* | (2006.01) | |

(52) U.S. Cl.
CPC .............. *C07C 51/09* (2013.01); *B01J 23/04* (2013.01); *C07C 51/412* (2013.01); *C07C 51/44* (2013.01); *C07C 59/01* (2013.01)

(58) Field of Classification Search
CPC ........ C07C 51/09; C07C 51/44; C07C 51/412
See application file for complete search history.

(56) References Cited

U.S. PATENT DOCUMENTS

| | | | | |
|---|---|---|---|---|
| 7,485,452 B2* | 2/2009 | Hwang | ...................... | C12P 7/62 435/280 |
| 8,535,399 B2* | 9/2013 | Chen | .......................... | C10L 1/02 44/388 |
| 2003/0088095 A1* | 5/2003 | Ishii | ....................... | C07C 29/143 544/59 |
| 2018/0282767 A1* | 10/2018 | Liao | ....................... | C12N 9/0006 |

OTHER PUBLICATIONS

Seebach et al. Direct Degradation of the Biopolymer Poly [(R)-3-Hydroxybutyric Acid] to (R)-3-hydroxybutanoic acid and its Methyl Ester. Organic Synthesis, Coll. vol. 9, p. 483; vol. 71, p. 39 (1993) (Year: 1998).*

* cited by examiner

*Primary Examiner* — Sikarl A Witherspoon
(74) *Attorney, Agent, or Firm* — Muncy, Geissler, Olds & Lowe, P.C.

(57) ABSTRACT

The instant disclosure discloses a method for preparing 3-hydroxybutyrate salts, which includes: (1) providing ethyl 3-hydroxybutyrate or methyl 3-hydroxybutyrate, and hydrolyzing through a basic catalyst to obtain 3-hydroxybutyric acid; (2) making 3-hydroxybutyric acid reacted with an inorganic base to give 3-hydroxybutyrate. The instant disclosure adopts salt formation in water to make the reaction proceed more thoroughly, and also to save reaction time, to reduce energy consumption and material loss, to improve product yield and to lower production cost. The concentration process of the roughing (i.e. crude preparation) of 3-hydroxybutyrate is omitted. During the series of processes of refining and concentrating 3-hydroxybutyrate with anhydrous ethanol, performing crystallization with adding acetone, filtering, washing and drying, the use of acetone as an organic solvent is decreased, material loss and energy consumption of the corresponding process is saved, production costs of 3-hydroxybutyrate is reduced as well. The heating processes of roughing and refining 3-hydroxybutyrate is decreased. The salt formation in water also avoids the problem that the produced 3-hydroxybutyrate is easy to absorb moisture, and the quality of the 3-hydroxybutyric acid salt is ensured.

9 Claims, 1 Drawing Sheet providing ethyl 3-hydroxybutyrate and hydrolyzing through a basic catalyst to obtain 3-hydroxybutyric acid
making 3-hydroxybutyric acid reacted with an inorganic base to give 3-hydroxybutyrate

METHOD FOR PREPARING 3-HYDROXYBUTYRATE SALTS

FIELD OF THE INVENTION

The instant disclosure relates to the field of chemical industry, in particular to a method for preparing 3-hydroxybutyrate salts.

BACKGROUND OF THE INVENTION

A 3-hydroxybutyric acid molecule has two functional groups, a hydroxyl group and a carboxyl group, which cause an integrated property of an alcohol and a carboxyl group, and make the 3-hydroxybutyric acid molecule an important pharmaceutical raw material and a pharmacological agent. (R)-3-hydroxybutyric acid is an R-isomer of the racemate of 3-hydroxybutyric acid, an optically active chiral compound, CAS No. 625-72-9. (R)-3-hydroxybutyric acid is a compound produced by metabolism of long-chain fatty acids in the liver in mammals. It is present as a major ketone body in plasma and peripheral tissues, and has excellent penetrating ability and rapid diffusion capability in human perivascular tissues, and can be used as a source of energy in most tissues of the body. In general, R-3-HB is present in the form of various salts. In addition to its nutritional function, (R)-3-hydroxybutyric acid has the function of treating many diseases, including: treating various diseases that benefit from increased levels of ketones (such as neurological disorders including epilepsy and myoclonus, and neurodegenerative diseases including Alzheimer's and dementia); reducing free radical damage (such as ischemia) by oxidizing coenzyme Q; enhancing metabolic efficiency (improvement of training efficiency and athletic performance, treatment of inadequate feeding, angina, myocardial infarction, etc.); treating diseases such as cancer, especially deseases related to brain cancer (such as astrocytoma); having good effects on glycemic disorders (such as type 1 diabetes, type 2 diabetes, hypoglycemia, ketosis, etc.); capable of being used to prevent osteopenia, osteoporosis, severe osteoporosis and related fractures. Based on these functions, (R)-3-hydroxybutyric acid and its salts can be used as food additives and medicines with great health and medicinal value.

The preparation of (R)-3-hydroxybutyric acid is mainly a chemical method and a microbial method. A disadvantage of the conventional chemical synthesis process is that the optical purity of the product is relatively low, i.e. the enantiomeric excess (ee value) is relatively low. Using the microbial fermentation method can directly obtain R-3-HB; or using microbial synthesis of poly R-3-HB followed by degradation of the polymer may also obtain R-3-HB. The product obtained from the microbiological method has a higher ee value. However, the complexity of the above processes and large investment in production lead to high cost and price of R-3-HB.

SUMMARY OF THE INVENTION

The instant disclosure is to solve the problems or disadvantages of high cost and low purity of the prepared of 3-hydroxybutyrate by chemical methods in the conventional related art.

In order to solve the above problems, the instant disclosure provides a method for preparing 3-hydroxybutyrate salts, which includes:

(1) providing ethyl 3-hydroxybutyrate or methyl 3-hydroxybutyrate, and hydrolyzing through a basic catalyst to obtain 3-hydroxybutyric acid; and (2) making 3-hydroxybutyric acid reacted with an inorganic base to give 3-hydroxybutyrate Further, the basic catalyst is sodium hydroxide, potassium hydroxide, calcium hydroxide, magnesium hydroxide, or lithium hydroxide.

Further, the molar ratio of ethyl 3-hydroxybutyrate or methyl 3-hydroxybutyrate, and the basic catalyst, is 1:2.5~4.5.

Further, the inorganic base is potassium hydroxide, calcium hydroxide, magnesium hydroxide, or sodium hydroxide, and the corresponding given 3-hydroxybutyrate is potassium 3-hydroxybutyrate, calcium 3-hydroxybutyrate, magnesium 3-hydroxybutyrate, or sodium 3-hydroxybutyrate.

Further, the molar ratio of 3-hydroxybutyric acid and the inorganic base is 2~2.1:1.5.

Further, the step (2) also includes adding activated carbon, and the activated carbon is weighing 10% of the weight of 3-hydroxybutyric acid.

Further, the step (1) specifically includes:

providing a reaction vessel, adding 200-300 g of water to the reaction vessel, and adding 100-150 g of ethyl 3-hydroxybutyrate or methyl 3-hydroxybutyrate with stirring; and adding 75-166 g of a basic catalyst and then raising the temperature to 35° C.-55° C. for 12-24 hours after the ethyl 3-hydroxybutyrate or methyl 3-hydroxybutyrate is completely dissolved.

Further, between the step (1) and the step (2), further includes:

after the reaction of the ethyl 3-hydroxybutyrate or methyl 3-hydroxybutyrate with the catalyst is completed, distilling to remove water under a temperature of 20° C.-40° C., lowering the temperature to 0° C., adding ethanol or isopropanol thereto, and sufficiently stirring and dispersing for 2-12 hours, lowering the temperature to below 0° C. for crystallization, and keeping the temperature between 0° C.-5° C. for 24 hours, separating by suction filtration, and washing solid content using ethanol or isopropanol and then drying under 35° C.-55° C. to obtain 3-hydroxybutyric acid.

Further, the step (2) specifically includes:

providing a reaction vessel, adding the 3-hydroxybutyric acid obtained from the step (1) to the reaction vessel, adding ethanol or isopropanol, and stirring to dissolve the 3-hydroxybutyric acid;

then adding potassium hydroxide, calcium hydroxide, magnesium hydroxide or sodium hydroxide, raising temperature to proceed reaction, and distilling to remove the ethanol or isopropanol after the reaction is completed; and cooling down to 0° C., adding isopropanol or ethanol, stirring well to disperse, cooling down to below 0° C. for crystallization, and keeping the temperature at 0° C.-5° C. for 12 hours, filtering by suction, washing solid contents with isopropanol or ethanol, and then drying at 35° C. to give 3-hydroxybutyrate.

Compared with the conventional related arts, the technical solutions according to the instant disclosure have the following advantages:

The instant disclosure adopts salt formation in water to make the reaction proceed more thoroughly, and also to save reaction time, to reduce energy consumption and material loss, to improve product yield and to lower production cost.

The concentration process of the roughing (i.e. crude preparation) of 3-hydroxybutyrate is omitted. During the series of processes of refining and concentrating 3-hydroxybutyrate with anhydrous ethanol, performing crystallization with adding acetone, filtering, washing and drying, the use of acetone as an organic solvent is decreased, material loss and energy consumption of the corresponding process is saved, production costs of 3-hydroxybutyrate is reduced as well.

The heating processes of roughing and refining 3-hydroxybutyrate is decreased. The salt formation in water also avoids the problem that the produced 3-hydroxybutyrate is easy to absorb moisture, and the quality of the 3-hydroxybutyric acid salt is ensured.

BRIEF DESCRIPTION OF THE DRAWINGS

The Sole FIGURE is a flow chart showing a process for producing 3-hydroxybutyrate in the first embodiment of the present invention.

DETAILED DESCRIPTION OF THE PREFERRED EMBODIMENTS

The above described objects, features and advantages of the instant disclosure will become more apparent from the aspects of the appended claims.

Example 1

Referring to the Sole FIGURE, the method for preparing 3-hydroxybutyrate salts, including:
(1) providing ethyl 3-hydroxybutyrate or methyl 3-hydroxybutyrate, and hydrolyzing through a basic catalyst to obtain 3-hydroxybutyric acid;
(2) making 3-hydroxybutyric acid reacted with an inorganic base to give 3-hydroxybutyrate In one embodiment, the basic catalyst is sodium hydroxide, potassium hydroxide, calcium hydroxide, magnesium hydroxide, or lithium hydroxide. The molar ratio of ethyl 3-hydroxybutyrate or methyl 3-hydroxybutyrate, and the basic catalyst, is 1:2.5~4.5.

In one embodiment, the molar ratio of 3-hydroxybutyric acid and the inorganic base is 2~2.1:1.5. The inorganic base is potassium hydroxide, calcium hydroxide, magnesium hydroxide, or sodium hydroxide, and the corresponding given 3-hydroxybutyrate is potassium 3-hydroxybutyrate, calcium 3-hydroxybutyrate, magnesium 3-hydroxybutyrate, or sodium 3-hydroxybutyrate.

Among the embodiments, the step (1) specifically includes:
providing a reaction vessel, adding 200-300 g of water to the reaction vessel, and adding 100-150 g of ethyl 3-hydroxybutyrate or methyl 3-hydroxybutyrate with stirring; and
adding 75-166 g of a basic catalyst and then raising the temperature to 35° C.-55° C. for 12-24 hours after the ethyl 3-hydroxybutyrate or methyl 3-hydroxybutyrate is completely dissolved.

The method according to the instant disclosure, between the step (1) and the step (2), further includes:
after the reaction of the ethyl 3-hydroxybutyrate or methyl 3-hydroxybutyrate with the catalyst is completed, distilling to remove water under a temperature of 20° C.~40° C., lowering the temperature to 0° C., adding ethanol or isopropanol thereto, and sufficiently stirring and dispersing for 2-12 hours, lowering the temperature to below 0° C. for crystallization, and keeping the temperature between 0° C.-5° C. for 24 hours, separating by suction filtration, and washing solid content using ethanol or isopropanol and then drying under 35° C.-55° C. to obtain 3-hydroxybutyric acid.

The step (2) also includes adding activated carbon, and the activated carbon is weighing 10% of the weight of 3-hydroxybutyric acid.

The step (2) specifically includes:
providing a reaction vessel, adding the 3-hydroxybutyric acid obtained from the step (1) to the reaction vessel, adding ethanol or isopropanol, and stirring to dissolve the 3-hydroxybutyric acid;
then adding potassium hydroxide, calcium hydroxide, magnesium hydroxide or sodium hydroxide, raising temperature to proceed reaction, and distilling to remove the ethanol or isopropanol after the reaction is completed; and
cooling down to 0° C., adding isopropanol or ethanol, stirring well to disperse, cooling down to below 0° C. for crystallization, and keeping the temperature at 0° C.-5° C. for 12 hours, filtering by suction, washing solid contents with isopropanol or ethanol, and then drying at 35° C. to give 3-hydroxybutyrate.

Compared to the related art, the technical solutions of the instant disclosure has the following advantages:

The instant disclosure adopts salt formation in water to make the reaction proceed more thoroughly, and also to save reaction time, to reduce energy consumption and material loss, to improve product yield and to lower production cost.

The concentration process of the roughing (i.e. crude preparation) of 3-hydroxybutyrate is omitted. During the series of processes of refining and concentrating 3-hydroxybutyrate with anhydrous ethanol, performing crystallization with adding acetone, filtering, washing and drying, the use of acetone as an organic solvent is decreased, material loss and energy consumption of the corresponding process is saved, production costs of 3-hydroxybutyrate is reduced as well.

The heating processes of roughing and refining 3-hydroxybutyrate is decreased. The salt formation in water also avoids the problem that the produced 3-hydroxybutyrate is easy to absorb moisture, and the quality of the 3-hydroxybutyric acid salt is ensured.

Example 2

200 g of water was added to the reaction vessel, and 130 g of ethyl 3-hydroxybutyrate or methyl 3-hydroxybutyrate was added thereto with stirring. After being completely dissolved, 166 g of lithium hydroxide was added, and then the temperature was raised to 35° C. to maintain a constant temperature. The reaction was proceeded for 24 hours.

After the reaction was completed, the water was removed via distillation at 20° C. or lower, then the temperature was lowered to 0° C. Ethanol was added, and the mixture was stirred for 2 hours. The temperature was further lowered to below 0° C. for crystallization, and then was kept at 0° C.-5° C. for 24 hours. The solid was washed with ethanol and dried at 35° C. to obtain 147 g of 3-hydroxybutyric acid in a yield of 90.1%.

The produced 3-hydroxybutyric acid was added to the reaction vessel, and ethanol was added thereto, stirred and dissolved. 105 g of calcium hydroxide was added, and the temperature was raised to 45° C. for proceeding reaction for 12 hours. After the reaction was completed, the ethanol was removed via distillation at 70° C. or lower, then the temperature was lowered to 0° C. Isopropanol was added, and the mixture was well stirred and dispersed. The temperature was further lowered to below 0° C. for crystallization, and then was kept between 0° C.-5° C. for 12 hours. The solid was separated by suction filtration, and washed with isopropanol, dried at 35° C. to obtain 177 g of calcium 3-hydroxybutyrate in a yield of 92%.

Example 3

300 g of water was added to the reaction vessel, and 150 g of ethyl 3-hydroxybutyrate or methyl 3-hydroxybutyrate was added thereto with stirring. After being completely dissolved, 156 g of potassium hydroxide was added, and then the temperature was raised to 45° C. to maintain a constant temperature. The reaction was proceeded for 24 hours.

After the reaction was completed, the water was removed via distillation at 40° C. or lower, then the temperature was lowered to 0° C. Isopropanol was added, and the mixture was well stirred and dispersed for 12 hours. The temperature was further lowered to below 0° C. for crystallization, and then was kept at 0° C.-5° C. for 24 hours. The solid was separated by suction filtration, and washed with ethanol, dried at 55° C. to obtain 176 g of 3-hydroxybutyric acid in a yield of 95.1%.

The produced 3-hydroxybutyric acid was added to the reaction vessel, and isopropanol was added thereto, stirred and dissolved. 125 g of magnesium hydroxide was added, and the temperature was raised to 55° C. for proceeding reaction for 12 hours. After the reaction was completed, the isopropanol was removed via distillation at 70° C. or lower, then the temperature was lowered to 0° C. Ethanol was added, and the mixture was well stirred and dispersed. The temperature was further lowered to below 0° C. for crystallization, and then was kept between 0° C.-5° C. for 12 hours. The solid was separated by suction filtration, and washed with ethanol, dried at 35° C. to obtain 185 g of magnesium 3-hydroxybutyrate in a yield of 97.2%.

Example 4

250 g of water was added to the reaction vessel, and 100 g of ethyl 3-hydroxybutyrate or methyl 3-hydroxybutyrate was added thereto with stirring. After being completely dissolved, 75 g of sodium hydroxide was added, and then the temperature was raised to 55° C. to maintain a constant temperature. The reaction was proceeded for 24 hours.

After the reaction was completed, the water was removed via distillation at 40° C. or lower, then the temperature was lowered to 0° C. Isopropanol was added, and the mixture was well stirred and dispersed for 12 hours. The temperature was further lowered to below 0° C. for crystallization, and then was kept at 0° C.-5° C. for 24 hours. The solid was separated by suction filtration, and washed with ethanol, dried at 55° C. to obtain 124 g of sodium 3-hydroxybutyrate in a yield of 95.1%

Example 5

250 g of water was added to the reaction vessel, and 100 g of ethyl 3-hydroxybutyrate or methyl 3-hydroxybutyrate was added thereto with stirring. After being completely dissolved, 40 g of potassium hydroxide was added, and then the temperature was raised to 55° C. to maintain a constant temperature. The reaction was proceeded for 24 hours.

After the reaction was completed, the water was removed via distillation at 40° C. or lower, then the temperature was lowered to 0° C. Isopropanol was added, and the mixture was well stirred and dispersed for 12 hours. The temperature was further lowered to below 0° C. for crystallization, and then was kept at 0° C.-5° C. for 24 hours. The solid was separated by suction filtration, and washed with ethanol, dried at 55° C. to obtain 123 g of potassium 3-hydroxybutyrate in a yield of 96.2%

Although the instant disclosure has been disclosed above, the instant disclosure is not limited thereto. Any changes and modifications may be made by those skilled in the art without departing from the spirit and scope of the invention, and the scope of the invention should be determined by the scope of the claims

What is claimed is:
1. A method for preparing 3-hydroxybutyrate salts, which is characterized by comprising:
   (1) providing ethyl 3-hydroxybutyrate or methyl 3-hydroxybutyrate, and hydrolyzing through a basic catalyst to obtain 3-hydroxybutyric acid;
   (2) making 3-hydroxybutyric acid reacted with an inorganic base to give 3-hydroxybutyrate.
2. The method for preparing 3-hydroxybutyrate salts as claimed in claim 1, wherein the basic catalyst is sodium hydroxide, potassium hydroxide, calcium hydroxide, magnesium hydroxide, or lithium hydroxide.
3. The method for preparing 3-hydroxybutyrate salts as claimed in claim 2, wherein the molar ratio of ethyl 3-hydroxybutyrate or methyl 3-hydroxybutyrate, and the basic catalyst, is 1:2.5~4.5.
4. The method for preparing 3-hydroxybutyrate salts as claimed in claim 1, wherein the inorganic base is potassium hydroxide, calcium hydroxide, magnesium hydroxide, or sodium hydroxide, and the corresponding given 3-hydroxybutyrate is potassium 3-hydroxybutyrate, calcium 3-hydroxybutyrate, magnesium 3-hydroxybutyrate, or sodium 3-hydroxybutyrate.
5. The method for preparing 3-hydroxybutyrate salts as claimed in claim 4, wherein the molar ratio of 3-hydroxybutyric acid and the inorganic base is 2~2.1:1.5.
6. The method for preparing 3-hydroxybutyrate salts as claimed in claim 5, wherein the step (2) further comprises adding activated carbon, and the activated carbon is weighing 10% of the weight of 3-hydroxybutyric acid.
7. The method for preparing 3-hydroxybutyrate salts as claimed in claim 1, wherein the step (1) further comprises:
   providing a reaction vessel, adding 200-300 g of water to the reaction vessel, and adding 100-150 g of ethyl 3-hydroxybutyrate or methyl 3-hydroxybutyrate with stirring;
   adding 75-166 g of a basic catalyst and then raising the temperature to 35° C.-55° C. for 12-24 hours after the ethyl 3-hydroxybutyrate or methyl 3-hydroxybutyrate is completely dissolved.
8. The method for preparing 3-hydroxybutyrate salts as claimed in claim 7, wherein between the step (1) and the step (2), further comprises:
   after the reaction of the ethyl 3-hydroxybutyrate or methyl 3-hydroxybutyrate with the catalyst is completed, distilling to remove water under a temperature of 20° C.~40° C., lowering the temperature to 0° C., adding ethanol or isopropanol thereto, and sufficiently stirring and dispersing for 2-12 hours, lowering the temperature to below 0° C. for crystallization, and keeping the temperature between 0° C.-5° C. for 24 hours, separating by suction filtration, and washing solid content using ethanol or isopropanol and then drying under 35° C.-55° C. to obtain 3-hydroxybutyric acid.
9. The method for preparing 3-hydroxybutyrate salts as claimed in claim 1, wherein the step (2) further comprises:

providing a reaction vessel, adding the 3-hydroxybutyric acid obtained from the step (1) to the reaction vessel, adding ethanol or isopropanol, and stirring to dissolve the 3-hydroxybutyric acid;

then adding potassium hydroxide, calcium hydroxide, magnesium hydroxide or sodium hydroxide, raising temperature to proceed reaction, and distilling to remove the ethanol or isopropanol after the reaction is completed;

cooling down to 0° C., adding isopropanol or ethanol, stirring well to disperse, cooling down to below 0° C. for crystallization, and keeping the temperature at 0° C.-5° C. for 12 hours, filtering by suction, washing solid contents with isopropanol or ethanol, and then drying at 35° C. to give 3-hydroxybutyrate.

* * * * *